United States Patent
Han et al.

(10) Patent No.: US 11,266,979 B2
(45) Date of Patent: *Mar. 8, 2022

(54) METHOD FOR PREPARING DEHYDROGENATION CATALYST FOR STRAIGHT CHAIN-TYPE LIGHT HYDROCARBON USING STABILIZED ACTIVE METAL COMPOSITE

(71) Applicant: HEESUNG CATALYSTS CORPORATION, Gyeonggi-do (KR)

(72) Inventors: Hyun-sik Han, Seoul (KR); Young-san Yoo, Gyeonggi-do (KR); Ho-Dong Kim, Gyeonggi-do (KR); Hyun-Woo Lee, Gyeonggi-do (KR)

(73) Assignee: HEESUNG CATALYSTS CORPORATION, Gyeonggi-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/774,180

(22) PCT Filed: Oct. 31, 2016

(86) PCT No.: PCT/KR2016/012352
§ 371 (c)(1),
(2) Date: May 7, 2018

(87) PCT Pub. No.: WO2017/082564
PCT Pub. Date: May 18, 2017

(65) Prior Publication Data
US 2018/0311645 A1      Nov. 1, 2018

(30) Foreign Application Priority Data
Nov. 10, 2015   (KR) .................. 10-2015-0157391

(51) Int. Cl.
*B01J 23/62* (2006.01)
*B01J 21/04* (2006.01)
(Continued)

(52) U.S. Cl.
CPC ............. *B01J 23/626* (2013.01); *B01J 21/04* (2013.01); *B01J 21/08* (2013.01); *B01J 23/42* (2013.01);
(Continued)

(58) Field of Classification Search
CPC .......... B01J 23/42; B01J 23/58; B01J 23/622; B01J 23/624; B01J 23/6525; B01J 21/04;
(Continued)

(56) References Cited

U.S. PATENT DOCUMENTS 3,864,284 A * 2/1975 Clippinger ............ C07C 5/3337
502/334
4,077,912 A    3/1978 Dolhyj et al.
(Continued)

FOREIGN PATENT DOCUMENTS

KR   10-2010-0078465 A   7/2010
KR   10-2014-0006909 A   1/2014
(Continued)

OTHER PUBLICATIONS

Zangeneh et al. (The influence of solvent on the performance of Pt-Sn/theta-Al2O3 propane dehydrogenation catalyst prepared by co-impregnation method, 2013, Fuel processing Technology, 109, pp. 118-123) (Year: 2013).*
(Continued)

*Primary Examiner* — Jun Li
(74) *Attorney, Agent, or Firm* — Ballard Spahr LLP

(57) ABSTRACT

The present invention relates to a method for preparing a dehydrogenation catalyst for a straight chain-type light hydrocarbon using a stabilized active metal composite, in (Continued)

other words, to a dehydrogenating catalyst for C3 to C4 straight chain hydrocarbons, and more specifically, to a technique for preparing a catalyst in which most of metal components contained in the catalyst are distributed evenly in a support in the form of an alloy rather than in the form of each separate metal, thereby exhibiting a high conversion rate and selectivity when used in dehydrogenation.

9 Claims, 3 Drawing Sheets

(51) Int. Cl.
  *C07C 5/333* (2006.01)
  *B01J 23/42* (2006.01)
  *B01J 29/04* (2006.01)
  *B01J 31/28* (2006.01)
  *B01J 21/08* (2006.01)

(52) U.S. Cl.
  CPC ............... *B01J 29/04* (2013.01); *B01J 31/28* (2013.01); *C07C 5/3337* (2013.01); *C07C 2521/04* (2013.01); *C07C 2523/62* (2013.01)

(58) Field of Classification Search
  CPC ........... B01J 21/08; B01J 29/04; B01L 21/04; B01L 21/08; B01L 29/04; C07C 5/3337
  See application file for complete search history.

(56) References Cited

U.S. PATENT DOCUMENTS

| | | | |
|---|---|---|---|
| 4,255,253 A | 3/1981 | Herrington et al. | |
| 4,716,143 A | 12/1987 | Imai | |
| 4,786,625 A | 11/1988 | Imai et al. | |
| 6,166,283 A * | 12/2000 | Bharadwaj | B01J 23/8966 585/658 |
| 6,177,381 B1 * | 1/2001 | Jensen | B01J 23/40 428/403 |
| 8,993,474 B2 * | 3/2015 | Choi | B01J 23/58 502/213 |
| 2005/0272965 A1 * | 12/2005 | Watson | C01B 3/386 585/658 |
| 2007/0123418 A1 | 5/2007 | Han | |
| 2009/0275792 A1 | 11/2009 | Vogel | |
| 2013/0261363 A1 | 10/2013 | Serban | |
| 2014/0274673 A1 * | 9/2014 | Kauffman | B01J 37/0213 502/213 |
| 2014/0323785 A1 | 10/2014 | Lande | |
| 2015/0158024 A1 | 6/2015 | Lande | |
| 2017/0151553 A1 * | 6/2017 | Lee | C07C 5/3337 |

FOREIGN PATENT DOCUMENTS

| | | |
|---|---|---|
| KR | 10-1527841 B1 | 6/2015 |
| WO | WO-2012/101567 A2 | 8/2012 |
| WO | WO-2017/082565 A1 | 5/2017 |

OTHER PUBLICATIONS

Wang, X. et al., Pt/Sn Intermettalic, Core/Shell and Alloy Nanoparticles: Colloidal Synthesis and structural Control. Chem Mater. 2013; 25:1400-7.

Zangeneh, F.T. et al., The Influence of Solvent on the Performance of Pt-Sn/θ-Al2O3 Propane Dehydrogenation Catalyst Prepared by Co-Impregnation Method. Fuel Process Technol. 2013; 109:118-23.

International Search Report dated Feb. 14, 2017 by the International Searching Authority for Patent Application No. PCT/KR2016/012353, which was filed on Oct. 31, 2016 and published as WO 2017/082565 on May 18, 2017 (Inventor—Han et al.; Applicant—Heesung Catalysts Corp.) (Translation Only—2 pages).

International Search Report dated Feb. 14, 2017 by the International Searching Authority for Patent Application No. PCT/KR2016/012352, which was filed on Oct. 31, 2016 and published as WO 2017/082564 on May 18, 2017 (Inventor—Han et al.; Applicant—Heesung Catalysts Corp.) (Translation Only—2 pages).

U.S. Appl. No. 15/774,140, filed May 7, 2018, Heesung Catalysts Corporation.

U.S. Appl. No. 16/611,061, filed Nov. 5, 2019, Heeseng Catalyst Corporation.

* cited by examiner

[FIG. 1]
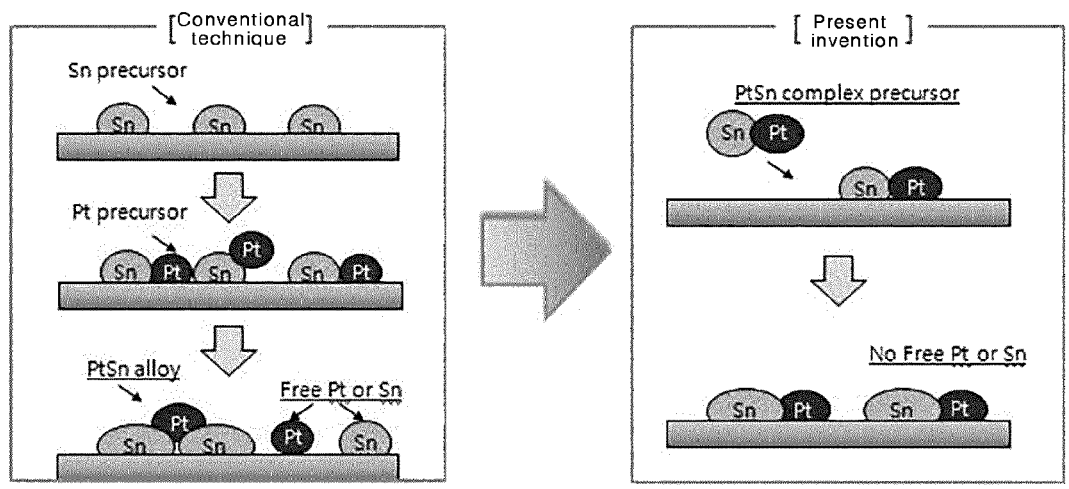
[FIG. 2]
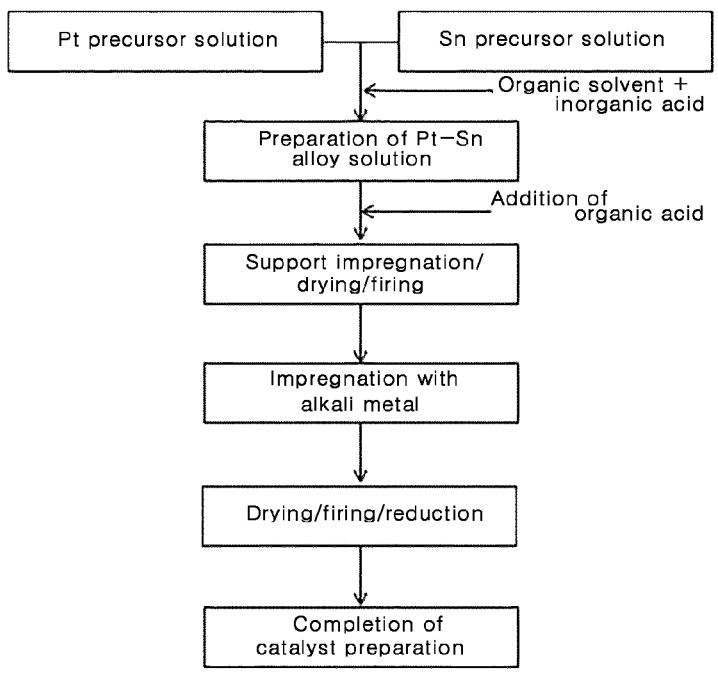

[FIG. 3]
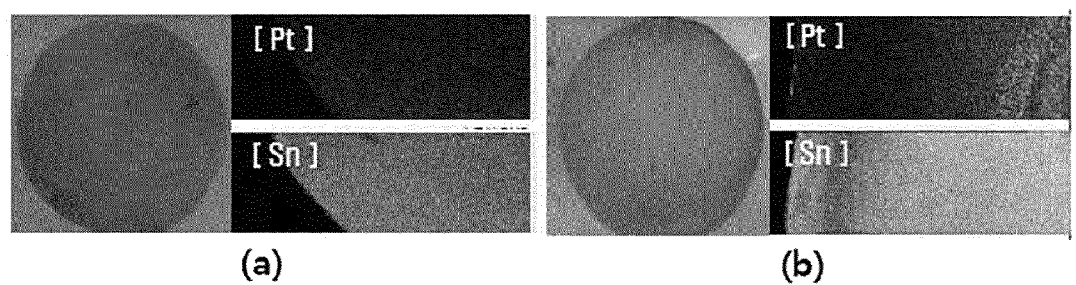
(a)          (b)
[FIG. 4]
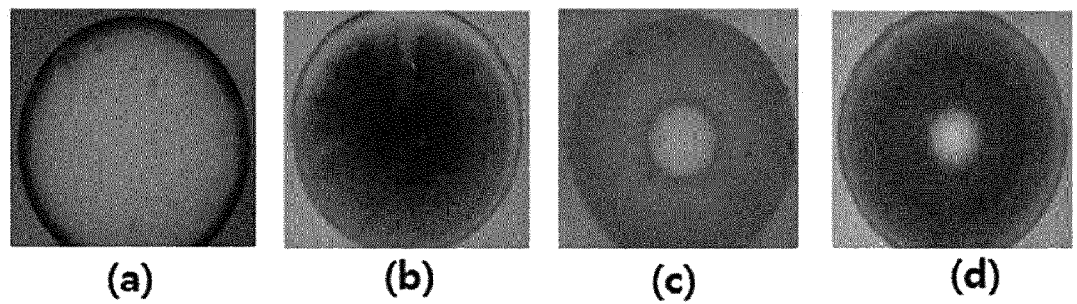
(a)      (b)      (c)      (d)

[FIG. 5]
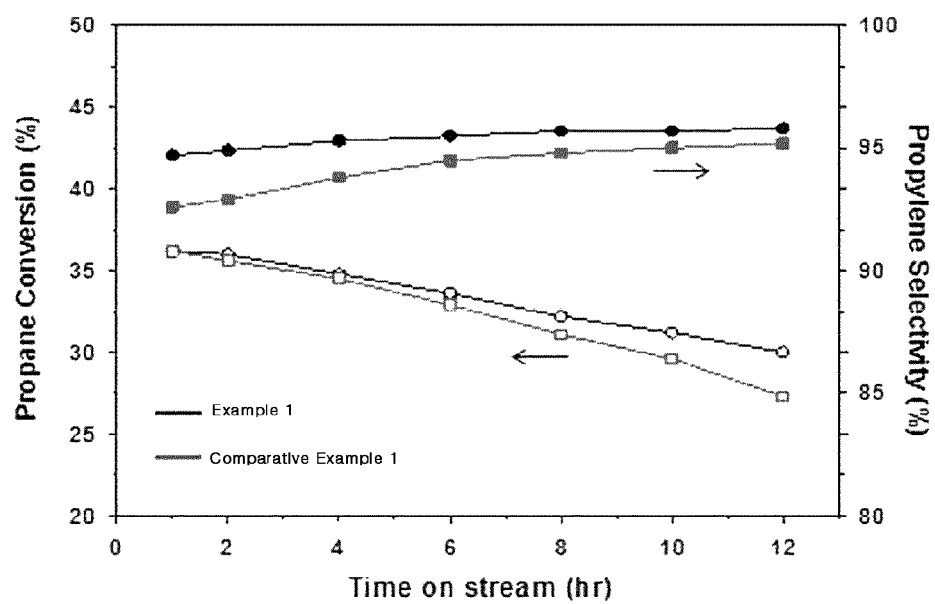

METHOD FOR PREPARING DEHYDROGENATION CATALYST FOR STRAIGHT CHAIN-TYPE LIGHT HYDROCARBON USING STABILIZED ACTIVE METAL COMPOSITE

CROSS-REFERENCE TO RELATED APPLICATIONS

This application is a U.S. National Phase Application of International Application No. PCT/KR2016/012352, filed Oct. 31, 2016, which claims priority to Korean Application No. 10-2015-0157391, filed Nov. 10, 2015, each of which are hereby incorporated by reference in their entirety.

TECHNICAL FIELD

The present invention relates to a method of preparing a dehydrogenation catalyst for a straight-chain-type light hydrocarbon using a stabilized active metal complex, namely a dehydrogenation catalyst for a $C_3$~$C_4$ straight-chain-type hydrocarbon. More particularly, the present invention relates to a technique for preparing a catalyst configured such that most metal components contained in the catalyst are uniformly distributed not in the form of individual metals but in the form of an alloy in a support, thereby exhibiting a high conversion rate and selectivity when used for dehydrogenation. In particular, the present invention is characterized by preparing a catalyst that exhibits high dispersibility and alloy properties using an organic solvent and an organic acid upon metal loading.

BACKGROUND ART

Typically, the dehydrogenation of light hydrocarbons is carried out using a catalyst configured such that active components, such as platinum, tin, and alkali metal components, are supported on a molded ball support having pores therein, such as gamma/theta/alpha alumina, zeolite, silica, and the like. The conversion rate and selectivity of dehydrogenation are important determinants of catalyst selection, and the catalyst is designed taking into consideration the following. For active site control, an alkali metal (Li, Na, K, etc.) is introduced because platinum dehydrogenation intensity is too strong, and tin is introduced in order to prevent catalyst activity from being deteriorated due to carbon deposition. It is also important to uniformly distribute the active sites in the spherical support in order to improve the reaction rate and durability. In general, the active material is uniformly distributed in spherical catalyst particles having a diameter of 2 mm in terms of material transfer and dispersion of the active material, thereby delaying the decrease in activity due to the increase in the overall conversion rate and the suppression of sintering at high temperatures. Meanwhile, since a $C_3$~$C_6$ hydrocarbon reaction proceeds at a high temperature, coke is generated in a very large amount even in a short reaction time. When the reactant is easily released to the outside of the catalyst after reaction through contact with the catalyst active sites, side reactions and coke deposition decrease. Therefore, the pores in the catalyst should be configured such that the incidence of micropores is decreased and macropores are mostly present. From this point of view, mainly useful as the catalyst support is an alumina support, the pore size of which may be adjusted. Specifically, gamma alumina is vulnerable to coke deposition due to its small pore size, and it is known that side reactions occur due to the acid sites of the support. For alpha-alumina, the extent of dispersion of the metal is inhibited to thus induce aggregation of metals, whereby good selectivity may be obtained but the overall conversion rate may be lowered. Furthermore, in the case where platinum in the catalyst is present alone, as the reaction progresses, rapid particle sintering takes place due to the high temperature, and poisoning readily occurs due to the coke generated after the reaction. As such, when tin is disposed beside the platinum, tin allows coke precursors adsorbed on the platinum to be easily moved to the support. Hence, the formation of a platinum-tin alloy throughout the catalyst is regarded as very important.

DISCLOSURE

Technical Problem

In the catalyst preparation according to a conventional technique, the thickness of active materials may be adjusted to a desired level, but platinum and tin are sequentially supported, and thus the platinum-tin alloy form depends only on the contact probability of the two active materials, and the alloy having the optimal platinum/tin molar ratio for a desired reaction is present together with platinum alone or other alloys having different platinum/tin molar ratios. Typically, when platinum, which provides active sites for the dehydrogenation reaction, and tin, which improves platinum stability, are provided in the form of an alloy, the best results may be achieved. However, the conventional technique is problematic in that side reactions occur during the reaction due to the presence of platinum alone or tin alone, in addition to the platinum-tin alloy.

Technical Solution

Therefore, the present invention provides a dehydrogenation catalyst for a light paraffinic hydrocarbon, in which active metals in a support are not present alone but are maintained uniform in the form of an alloy, thus significantly increasing the paraffin conversion rate, olefin selectivity and durability, and also provides a method of preparing the same. In the present invention, the fact that active metals are individually present in the support when directly supported to the support, as in the conventional technique, thus resulting in an undesirable platinum-tin alloy ratio, is recognized, and thus active materials, namely platinum and tin, are made in the form of an alloy using an organic solvent from the initial impregnation step and are also uniformly distributed in the support by the addition of an organic acid, thereby completing a catalyst.

Advantageous Effects

According to the present invention, the consistent distribution of platinum and tin can be achieved, and platinum and tin are present in the form of an alloy at a consistent platinum/tin molar ratio by reduction, thereby minimizing the incidence of platinum alone and alloys having different platinum/tin molar ratios, ultimately improving durability and selectivity.

DESCRIPTION OF DRAWINGS

FIG. 1 shows the key process of the present invention compared to a conventional technique;

FIG. 2 is a flowchart showing the processing steps of the present invention;

FIG. 3 shows video microscopy images and electron probe microanalysis (EPMA) images of the catalysts of Example 1 according to the present invention and Comparative Example 1;

FIG. 4 shows video microscopy images of the catalysts of Examples 2 to 4 according to the present invention and Comparative Example 2; and FIG. 5 shows the results of evaluation of activity of the catalysts of Example 1 and Comparative Example 1 over time.

BEST MODE

The present invention pertains to a dehydrogenation catalyst for a $C_3$~$C_4$ straight-chain-type hydrocarbon, and to a technique for preparing a catalyst configured such that metal components contained in the catalyst are uniformly distributed in the form of an alloy in a support. The catalyst for dehydrogenation of a light hydrocarbon undergoes a reaction at a relatively high temperature compared to a heavy hydrocarbon, whereby a large amount of coke is produced due to pyrolysis and other side reactions. Accordingly, the rate of material transfer depending on the pore size and the pore volume of the support may be regarded as the main factor during the corresponding reaction. Also, the active metals of the catalyst have to be uniformly distributed throughout the catalyst to thus maximally decrease the rate of deactivation due to coke. Also, when platinum is present alone in the support, it is easily covered with coke, and thus a predetermined amount of tin always has to be present thereraround. When the catalyst satisfying the above three conditions is used, side reactions may be suppressed during dehydrogenation, and thus durability is increased, and furthermore, the conversion rate and selectivity of the catalytic reaction may be improved. The present inventors have confirmed the preparation of a dehydrogenation catalyst for a light paraffinic hydrocarbon, in which active metals in the support are not present alone but are maintained uniform in the form of an alloy, thereby greatly increasing the paraffin conversion rate, olefin selectivity and durability. FIG. 1 shows the key process of the present invention compared to the conventional technique, and FIG. 2 shows the flowchart of the process of the present invention. The method of the present invention as shown in FIG. 2 is comprehensively described below.

1) Preparation of Stabilized Platinum-Tin Complex Solution

A platinum-tin complex solution enables the easy precipitation of platinum in air due to the high reducibility of tin. In the preparation of a complex solution, the selection of a solvent is very important. When water is used as the solvent, platinum is reduced by tin and thus the platinum-tin precursor solution becomes very unstable, and consequently platinum particles may precipitate, and thus the use thereof as the precursor is impossible. In the present invention, the precursor solution is made stable over time using a solvent that may prevent tin reduction. Specifically, during the mixing of platinum and tin precursors, these precursors are added to an organic solvent so as not to break a platinum-tin complex, and hydrochloric acid is added to thus prepare a solution in an acid atmosphere. Next, in order to increase the rate of penetration into the support, an organic acid is further added. As the organic solvent, any one or two selected from among water, methanol, ethanol, butanol, acetone, ethyl acetate, acetonitrile, ethylene glycol, triethylene glycol, glycol ether, glycerol, sorbitol, xylitol, dialkyl ether, and tetrahydrofuran may be sequentially used, or may be used in combination. As the organic acid, any one or two selected from among carboxylic acids, such as formic acid, acetic acid, glycolic acid, glyoxylic acid, oxalic acid, propionic acid, and butyric acid, may be used in combination. During the preparation of the platinum-tin complex solution, aging in an inert gas atmosphere is performed to thus suppress decomposition by oxygen and realize stabilization. Here, the inert gas may include nitrogen, argon, and helium, and preferably nitrogen gas.

2) Preparation of Catalyst Using Stabilized Platinum-Tin Complex Solution and Alkali Metal The support is used by subjecting gamma-alumina to phase transformation into theta-alumina through thermal treatment at 1000 to 1050° C. for 5 hr in a firing furnace in order to increase the pore size and pore volume thereof. The thermal treatment temperature is closely associated with the crystal phase of the support and the pore structure thereof. If the thermal treatment temperature is lower than 1000° C., alumina has a crystal phase in which gamma and theta forms are mixed, and the pore size of the support is small, thus decreasing the rate of diffusion of the reactant in the support. On the other hand, if the thermal treatment temperature is higher than 1050° C., alumina has a crystal phase in which theta and alpha forms are mixed. As such, the pore size is set so as to be favorable for the reaction, but during the loading of active metals, the extent of dispersion of active metals distributed on alpha-alumina may decrease. During the loading of active metals, a platinum-tin complex solution in an amount corresponding to the total pore volume of the support is prepared, and is used to impregnate the support using a spraying process. After the impregnation process, the catalyst is homogenized while the catalyst is allowed to flow in a nitrogen atmosphere, whereby the active metal concentrations on the surface of the catalyst are made the same, followed by drying at 100 to 150° C. for 24 hr. After the drying, the organic material is removed at 200 to 400° C. in a nitrogen atmosphere, followed by firing at 400 to 700° C. in air. If thermal treatment is carried out at a temperature of less than 400° C., the supported metal may not change into metal oxide species. On the other hand, if thermal treatment is carried out at a temperature of higher than 700° C., intermetallic aggregation may occur, and the activity of the catalyst is not high relative to the amount thereof. After the firing, in order to suppress side reactions of the catalyst, the loading of an alkali metal is carried out. Specifically, potassium is loaded to the pores in the support using the same spraying process as in the platinum-tin complex solution, dried at 100 to 150° C. for 24 hr, and then fired at 400 to 700° C. in air. Finally, after the firing, a reduction process is carried out at 400 to 600° C. using a hydrogen/nitrogen mixed gas (4%/96%~100%/0%), thereby yielding a catalyst. During the reduction process, if the reduction temperature is lower than 400° C., metal oxide species cannot be completely reduced, and two or more kinds of metal particles may be individually present, rather than in the form of an alloy. On the other hand, if the reduction temperature is higher than 600° C., aggregation and sintering of two or more kinds of metal particles may occur, whereby the incidence of active sites may decrease and catalytic activity may be lowered. The reduction process is carried out not in a heating reduction manner with hydrogen gas from a heating step, but in a high-temperature reduction manner in which a nitrogen atmosphere is maintained until the temperature reaches the corresponding temperature, after which hydrogen gas is introduced at the corresponding temperature.

The performance of the catalyst thus prepared was evaluated as follows. A method of converting a light paraffin hydrocarbon into an olefin may be conducted in a manner in which the dehydrogenation catalyst according to the present invention is used, and a hydrocarbon having 2 to 5 carbon atoms, and preferably 3 to 4 carbon atoms, including paraffin, iso-paraffin, and alkyl aromatic material, is diluted with hydrogen, and may then be subjected to a gaseous reaction at 500~680° C., preferably 570° C., 0~2 atm, preferably 1.5 atm, and a LHSV (Liquid Hourly Space Velocity) of a paraffin hydrocarbon of 1~40 $h^{-1}$, and preferably 15~30 $h^{-1}$. The reactor for producing olefin through dehydrogenation is not particularly limited, and a fixed-bed catalytic reactor in which the catalyst is packed may be used. Also, since the dehydrogenation reaction is endothermic, it is important that the catalytic reactor be maintained adiabatic at all times. The dehydrogenation reaction of the present invention should be carried out under conditions in which the reaction temperature, pressure and liquid space velocity are maintained within appropriate ranges. If the reaction temperature is low, the reaction does not occur, and if the reaction temperature is too high, the reaction pressure increases in proportion thereto, and moreover, side reactions such as coke production, cracking, and the like, may occur.

Example 1: Preparation of Catalyst Using Co-Impregnation with Platinum and Tin in the Presence of Organic Solvent The support of Example 1 was used after phase transformation of a gamma-alumina support (made by BASF, Germany, specific surface area: 210 $m^2/g$, pore volume: 0.7 $cm^3/g$, average pore size: 8.5 nm) into theta-alumina through firing at 1020° C. for 5 hr. The phase-transformed theta-alumina had physical properties such as a specific surface area of 95 $m^2/g$, a pore volume of 0.4 $cm^3/g$, and an average pore size of 12 nm. A platinum precursor, chloroplatinic acid ($H_2PtCl_6$), and a tin precursor, tin chloride ($SnCl_2$), were used, and chloroplatinic acid in an amount of 0.4 wt % based on the total weight of the catalyst and tin chloride at a platinum/tin molar ratio of 1.5 were mixed in a nitrogen atmosphere. Next, the platinum-tin mixture was added to a solvent in an amount corresponding to the total pore volume of the support and thus dissolved. As the solvent, 95 wt % ethanol and 5 wt % hydrochloric acid were used. In order to impart flowability of the platinum-tin alloy solution in the support, glyoxylic acid was further mixed in an amount of 3 wt % based on the total amount of the solvent. The phase-transformed theta-alumina support was impregnated with the prepared platinum-tin complex solution using an incipient wetness process. The platinum-tin-supported composition was dried at 100° C. for 24 hr and then thermally treated at 600° C. for 4 hr in air, and thus active metals were immobilized. Next, potassium nitride ($KNO_3$) in an amount of 0.7 wt % based on the total weight of the catalyst was supported to the pores in the alumina containing platinum and tin using an incipient wetness process, and the metal-supported composition was thermally treated at 570° C. for 4 hr in air to thus prepare a metal-supported catalyst. The catalyst was reduced stepwise in a manner in which the temperature was elevated to 570° C. in a nitrogen atmosphere and then maintained for 4 hr using a hydrogen/nitrogen mixed gas (4%/96%), thereby preparing a catalyst.

Example 2: Preparation of Catalyst Using Co-Impregnation with Platinum and Tin in the Presence of Organic Solvent The catalyst of Example 2 was prepared in the same manner as in Example 1, with the exception that upon the preparation of the tin-platinum complex solution, only ethanol was used as the solvent.

Example 3: Preparation of Catalyst Using Co-Impregnation with Platinum and Tin in the Presence of Organic Solvent The catalyst of Example 3 was prepared in the same manner as in Example 1, with the exception that upon the preparation of the tin-platinum complex solution, ethanol and hydrochloric acid at a weight ratio of 80:20 were used as the solvent.

Example 4: Preparation of Catalyst Using Co-Impregnation with Platinum and Tin in the Presence of Organic Solvent The catalyst of Example 4 was prepared in the same manner as in Example 1, with the exception that upon the preparation of the tin-platinum complex solution, glyoxylic acid was not added to the solvent.

Comparative Example 1: Preparation of Catalyst Using Sequential Impregnation with Platinum and Tin in the Absence of Organic Solvent The support of Comparative Example 1 was used after phase transformation of gamma-alumina into theta-alumina through firing at 1020° C. for 5 hr, as in Example 1. As a platinum precursor, chloroplatinic acid ($H_2PtCl_6$) was used, and platinum in an amount of 0.4 wt % based on the total weight of the catalyst was diluted with deionized water in an amount corresponding to the total pore volume of the support, and was then used to impregnate the support through an incipient wetness process. The platinum-supported composition was thermally treated at 600° C. for 4 hr in air, and thus the active metal was immobilized. Furthermore, tin chloride ($SnCl_2$) at a platinum/tin molar ratio of 1.5, serving as a tin precursor, was supported to the pores in the platinum-supported alumina using an incipient wetness process, and the metal-supported composition was thermally treated at 600° C. in air to thus immobilize the active metal. Next, potassium nitride ($KNO_3$) in an amount of 0.7 wt % based on the total weight of the catalyst was supported to the pores in the alumina containing platinum and tin using an incipient wetness process, and the metal-supported composition was thermally treated at 570° C. for 4 hr in air, thus preparing a metal-supported catalyst. The catalyst was reduced in a manner in which the corresponding temperature was maintained for 4 hr using a hydrogen/nitrogen mixed gas (4%/96%), thereby yielding a catalyst.

Comparative Example 2: Preparation of Catalyst Using Co-Impregnation with Platinum and Tin in the Absence of Organic Solvent The catalyst of Comparative Example 2 was prepared in the same manner as in Example 1, with the exception that upon the preparation of the platinum-tin complex solution, deionized water was used as the solvent in lieu of ethanol/glyoxylic acid.

FIG. 3 shows the video microscopy images and EPMA images of the catalysts of Example 1 according to the present invention and Comparative Example 1. The images of (a) show the cross-section of the catalyst of Example 1 prepared using the tin-platinum alloy solution and the distribution of platinum and tin in the support, and the images of (b) show the cross-section of the catalyst of Comparative Example 1 prepared using individual platinum and tin solutions and the distribution of platinum and tin in the support. Based on the results of analysis of the metal distribution in the catalyst, in the catalyst of Example 1, prepared using the platinum-tin alloy solution, metals were distributed in a very uniform arrangement, but in the catalyst of Comparative Example 1, prepared using the conventional process, platinum and tin were locally non-uniform, and thus it is considered that the PtSn alloy ratio is low and the platinum/tin molar ratio varies depending on the position of the catalyst.

FIG. 4 shows the video microscopy images of the catalysts of Examples 2 to 4 according to the present invention and Comparative Example 2. The image of (a) shows the cross-section of the catalyst of Example 2, prepared using the platinum-tin alloy solution in which only the ethanol is used as the solvent, the image of (b) shows the cross-section of the catalyst of Example 3, prepared using the platinum-tin alloy solution in which the ethanol/hydrochloric acid ratio is varied, the image of (c) shows the cross-section of the catalyst of Example 4, prepared using the platinum-tin alloy solution in which glyoxylic acid is not added, and the image of (d) shows the cross-section of the catalyst of Comparative Example 2, prepared using the platinum-tin alloy solution in the absence of the organic solvent. Based on the results of analysis of the metal distribution in the catalyst, in Example 2, in which hydrochloric acid was not added to the solution, the outside of the support was impregnated with the active metals, and in Example 3, in which an excess of hydrochloric acid was added to the solution, the outer active metals were introduced into the support, and thus the inner active metal concentration was increased. In Example 4, in which glyoxylic acid was not added, complete inner saturation of the support with the active metals was not realized. However, when the deionized water was used as the solvent for the platinum-tin alloy solution, as shown in FIG. 4(d), the inner active metals included a high-concentration metal layer in the middle position, and were thus non-uniformly distributed.

Test Example 1: Evaluation of Catalyst Performance

In order to measure the activity of the catalyst, a dehydrogenation reaction was carried out, and a fixed-bed reaction system was used as a reactor. Specifically, 3.0 g of the catalyst was placed in a tube-shaped reactor, and hydrogen gas was allowed to uniformly flow at a rate of 100 cc/min so that the catalyst was reduced at 570° C. for 1 hr. Subsequently, the temperature of the reactor was uniformly maintained at 570° C., after which a gas mixture of propane and hydrogen at a volume ratio of 1:1 as the reaction feed was continuously supplied into the reactor at a constant rate, and the liquid space velocity was set to 21 $h^{-1}$. The reaction pressure was maintained at 1.5 atm using a pressure regulator. The material produced after the reaction for 3 hr was cooled to a temperature of 4° C. or less and stored, and the product taken out of the reactor was transferred to a gas chromatograph through a line wound with a thermal line, and quantitative analysis was carried out using an FID (Flame Ionization Detector) and a TCD (Thermal Conductivity Detector). The propane conversion rate and propylene selectivity of the product were calculated based on the following equations. The properties of the products using the above catalysts are summarized in Table 1 below.

Propane conversion rate (%)=[propane mol before reaction−propane mol after reaction]/[propane mol before reaction]×100

Propylene selectivity (%)=[propylene mol in product]/[product mol]×100

Propylene yield (%)=[propane conversion rate]×[propylene selectivity]/100

The results of activity test of the catalysts of Examples 1 to 4 and Comparative Examples 1 and 2 are shown in Table 1 below.

TABLE 1

| No. | Metal distribution in support (800 μm radius) | | Propane conversion rate (%) | | Propylene selectivity (%) | | Propylene yield (%) | |
|---|---|---|---|---|---|---|---|---|
| | Platinum (μm) | Tin (μm) | 1 hr | 3 hr | 1 hr | 3 hr | 1 hr | 3 hr |
| Example 1 | Outer 800 | Outer 800 | 36.2 | 35.9 | 94.7 | 94.9 | 34.3 | 34.1 |
| Example 2 | Outer 70 | Outer 70 | 36.4 | 33.1 | 94.2 | 94.4 | 34.3 | 31.2 |
| Example 3 | Inner 600 | Outer 800 | 34.3 | 33.5 | 93.5 | 93.6 | 32.1 | 31.4 |
| Example 4 | Outer 600 | Outer 600 | 35.9 | 34.9 | 93.6 | 93.8 | 33.6 | 32.7 |
| Comparative Example 1 | Outer 800 | Outer 800 | 36.2 | 35.0 | 92.6 | 92.9 | 33.5 | 32.5 |
| Comparative Example 2 | Outer 700 | Outer 400 | 36.4 | 34.3 | 90.4 | 90.8 | 32.9 | 31.1 |

Conclusion

As is apparent from Table 1, the catalyst of Example 1, in which platinum-tin was uniformly alloyed, exhibited the highest initial activity and durability. When the thickness of the platinum-tin alloy in the support was low (Examples 2 and 4), the initial conversion rate was high, but rapid deactivation occurred over time. Although not theoretically limited, platinum active sites present on the catalyst were distributed outside at high density, and thus platinum dispersibility was lowered, and most of the active sites were exposed to a large amount of coke produced during the reaction, and after 3 hr, the overall conversion rate was lowered, from which the durability of the catalyst is regarded as poor. Upon the preparation of the platinum-tin alloy solution, when a predetermined amount or more of hydrochloric acid was contained (Example 3), tin was uniformly distributed in the support, but platinum was excessively diffused inwards, and thus the platinum concentration on the surface of the catalyst was considerably lowered, whereby the overall conversion rate was decreased. In Comparative Example 1, both platinum and tin were uniformly distributed in the catalyst, but poor durability resulted. This is deemed to be because the platinum/tin molar ratio was locally varied and thus an overall non-uniform reaction occurred, thus lowering selectivity. Hence, the initial activity was the same as in Example 1 but after 3 hr, considerable deactivation occurred, and thus low propylene yield was observed. In Comparative Example 2, due to the platinum present alone in the catalyst, side reactions such as cracking or the like occurred to a considerable extent and thus the conversion rate was increased but the propylene selectivity was lowered. Accordingly, the distribution of platinum and tin and the alloy state thereof can be found to have a great influence on the conversion rate and selectivity in the propane dehydrogenation. Moreover, in order to exhibit high catalytic activity, upon the preparation of the platinum-tin alloy solution, the inclusion of organic solvent/hydrochloric acid/organic acid and the ratio thereof are regarded as important.

Test Example 2: Evaluation of Long-Term Activity of Catalyst

The reactant was dehydrogenated for 12 hr using the catalysts of Example 1 and Comparative Example 1 under the same conditions as in Test Example 1. The results are shown in FIG. 5 and Table 2 below.

Table 2: Results of evaluation of activity of catalyst of Example 1 and Comparative Example 1

TABLE 2

| T.O.S (hr) | Propane conversion rate (%) | | Propylene selectivity (%) | | Propylene yield (%) | |
|---|---|---|---|---|---|---|
| | Example 1 | Comparative Example 1 | Example 1 | Comparative Example 1 | Example 1 | Comparative Example 1 |
| 1 | 36.2 | 36.2 | 94.7 | 92.6 | 34.3 | 33.5 |
| 2 | 36 | 35.6 | 94.9 | 92.9 | 34.2 | 33.1 |
| 4 | 34.8 | 34.5 | 95.3 | 93.8 | 33.2 | 32.4 |
| 6 | 33.6 | 32.9 | 95.5 | 94.5 | 32.1 | 31.1 |
| 8 | 32.2 | 31.1 | 95.7 | 94.8 | 30.8 | 29.5 |
| 10 | 31.2 | 29.6 | 95.7 | 95 | 29.9 | 28.1 |
| 12 | 30 | 27.3 | 95.8 | 95.2 | 28.7 | 26.0 |

Conclusion

As is apparent from Table 2, initial conversion rate and selectivity of the two catalysts started from the same levels, but the catalyst of Example 1 was found to exhibit superior propane conversion rate and durability compared to the catalyst of Comparative Example 1 over time.

The invention claimed is:

1. A dehydrogenation catalyst for use in dehydrogenation of a hydrocarbon gas, wherein the dehydrogenation catalyst is a uniform dehydrogenation catalyst configured such that platinum, tin, and an alkali metal are supported to a support consisting of theta-alumina, wherein the platinum and the tin are present in a form of an alloy at a consistent platinum/tin molar ratio in the catalyst, and wherein the alloy of platinum and tin is uniformly distributed from an outer surface of the theta-alumina support to a center of the theta-alumina support.

2. The dehydrogenation catalyst of claim 1, wherein the platinum/tin molar ratio is 1.5-5.

3. The dehydrogenation catalyst of claim 1, wherein the theta-alumina support is spherical.

4. The dehydrogenation catalyst of claim 1, wherein the uniform dehydrogenation catalyst is configured such that, based on a total weight of the catalyst, 0.1-1.0 wt % of the platinum, 0.05-0.75 wt % of the tin, and 0.1-2.0 wt % of the alkali metal are supported to the theta-alumina support.

5. The dehydrogenation catalyst of claim 1, wherein the alkali metal is potassium.

6. A method of dehydrogenating a hydrocarbon, comprising bringing a hydrocarbon gas having 2 to 6 carbon atoms into contact with the dehydrogenation catalyst of claim 1 subjected to a gaseous dehydrogenation reaction at temperature of 500-680° C., pressure of 0-2 atm, a Liquid Hourly Space Velocity (LVHS) of 1 to 40 $h^{-1}$ to produce olefin.

7. A method of making the dehydrogenation catalyst of claim 1, comprising the steps of:
 a) preparing a platinum/tin alloy solution by adding platinum and tin precursors to an organic solvent, and further adding to the resulting mixture hydrochloric acid and an organic acid;
 b) preparing a theta-alumina support;
 c) impregnating the platinum/tin alloy solution resulting from step a) into the theta-alumina support of step b) using a spraying process, then drying the support and firing the dried support;
 d) loading the fired support with an alkali metal to prepare an alkali metal impregnated support; and
 e) drying the alkali metal impregnated support; firing the dried alkali metal impregnated support, and then reducing the fired alkali metal impregnated support using a hydrogen/nitrogen mixed gas to obtain the dehydrogenation catalyst.

8. The method of claim 7, wherein the organic solvent is one or two selected in the group consisting of water, methanol, ethanol, butanol, acetone, ethyl acetate, acetonitrile, ethylene glycol, triethylene glycol, glycol ether, glycerol, sorbitol, xylitol, dialkyl ether, tetrahydrofuran and their combinations.

9. The method of claim 7, wherein the organic acid is one or two selected in the group consisting of carboxylic acids, such as formic acid, acetic acid, glycolic acid, glyoxylic acid, oxalic acid, propionic acid, butyric acid and their combinations.

* * * * *